(12) United States Patent
Dairkee et al.

(10) Patent No.: US 7,056,663 B2
(45) Date of Patent: Jun. 6, 2006

(54) PROGNOSTIC METHODS FOR BREAST CANCER

(75) Inventors: Shanaz H. Dairkee, Orinda, CA (US); Zheng Li, Hayward, CA (US)

(73) Assignee: California Pacific Medical Center, San Francisco, CA (US)

( * ) Notice: Subject to any disclaimer, the term of this patent is extended or adjusted under 35 U.S.C. 154(b) by 736 days.

(21) Appl. No.: 09/816,460

(22) Filed: Mar. 23, 2001

(65) Prior Publication Data

US 2003/0087235 A1 May 8, 2003

(51) Int. Cl.
*C12Q 1/68* (2006.01)
(52) U.S. Cl. .......................................................... 435/6
(58) Field of Classification Search .................... 435/6, 435/91.1, 91.2; 536/23.1, 24.33, 24.32, 24.3
See application file for complete search history.

(56) References Cited

U.S. PATENT DOCUMENTS

| 2001/0039015 A1 | 11/2001 | Sauter |
| 2002/0055096 A1 | 5/2002 | Deng et al. |

FOREIGN PATENT DOCUMENTS

WO    WO 98/17828 A1    4/1998

OTHER PUBLICATIONS

Deng et al. Loss of Heterozygosity in Normal Tissue Adjacent to Breast Carcinomas. Science, vol. 274, pp. 2057-2059, Dec. 1996.*
Blumenstein et al. International Journal of Oncology, vol. 21, pp. 447-450, 2002.*
Ali, Iqbal Unnisa, et al., "Presence of Two Members of c-erbA Receptor Gene Family (C-erbAβ and c-erbA2) in Smallest Region of Somatic Homozygosity on Chromosome 3p21-p25 in Human Breast Carcinoma," *Journal of the National Cancer Institute*, Dec. 6, 1989, pp. 1815-1820, vol. 81, No. 23.
Chen, Ling-Chun, et al., "Heterogeneity for Allelic Loss in Human Breast Cancer," *Journal of the National Cancer Institute*, Apr. 1, 1992, pp. 506-510, vol. 84, No. 7.
Chen, Ling-Chun, et al., "Deletion of Two Separate Regions on Chromosome 3p in Breast Cancers," *Cancer Research*, Jun. 1, 1994, pp. 3021-3024, vol. 54, No. 11.
Deng, Guoren, et al., "Loss of Heterozygosity and *p53* Gene Mutations in Breast Cancer," *Cancer Research*, Jan. 15, 1994, pp. 499-505, vol. 54, No. 2.
Deng, Guoren, et al., "Loss of Heterozygosity in Normal Tissue Adjacent to Breast Carcinomas," *Science*, Dec. 20, 1996, vol. 274.
Matsumoto, Satoshi, et al., "Detailed Deletion Mapping of Chromosome Arm 3p in Breast Cancers: A 2-cM Region on 3p14.3-21.1 and a 5-cM Region on 3p24.3-25.1 Commonly Deleted in Tumors," *Genes, Chromosomes and Cancer*, 1997, pp. 268-274, vol. 20.
Matsumoto, Satoshi, et al., "Loss of heterozygosity at 3p24-p25 as a prognostic factor in breast cancer," *Cancer Letters*, Apr. 28, 2000, pp. 63-69, vol. 152, No. 1.
O'Connell, Peter, et al., "Molecular genetic studies of early breast cancer evolution," *Breast Cancer Research and Treatment*, 1994, pp. 5-12, vol. 32.

* cited by examiner

*Primary Examiner*—Kenneth R. Horlick
*Assistant Examiner*—Cynthia Wilder

(57) ABSTRACT

Methods of determining the likelihood of the re-occurrence of tumors and of determining the aggressiveness of post-surgical treatment are provided which rely on analysis of a loss of heterogeneity at the particular chromosomal locus 3p24.3. Loss of expression or hypermethylation of the thyroid hormone receptor β1 gene is also predictive of an increased re-occurrence of tumors.

17 Claims, No Drawings

SEQUENCE LISTING

<160> NUMBER OF SEQ ID NOS: 47

<210> SEQ ID NO 1
<211> LENGTH: 21
<212> TYPE: DNA
<213> ORGANISM: Artificial Sequence
<220> FEATURE:
<223> OTHER INFORMATION: synthetic primer

<400> SEQUENCE: 1
gaacagtcgt cgccacatct c                21

```
<210> SEQ ID NO 2
<211> LENGTH: 19
<212> TYPE: DNA
<213> ORGANISM: Artificial Sequence
<220> FEATURE:
<223> OTHER INFORMATION: synthetic primer

<400> SEQUENCE: 2
tgagctccca ttcctcgtc                                               19

<210> SEQ ID NO 3
<211> LENGTH: 24
<212> TYPE: DNA
<213> ORGANISM: Artificial Sequence
<220> FEATURE:
<223> OTHER INFORMATION: synthetic primer

<400> SEQUENCE: 3
tgatgacatc aagaaggtgg tgaa                                         24

<210> SEQ ID NO 4
<211> LENGTH: 23
<212> TYPE: DNA
<213> ORGANISM: Artificial Sequence
<220> FEATURE:
<223> OTHER INFORMATION: synthetic primer

<400> SEQUENCE: 4
tccttggagg ccatgtgggc cat                                          23

<210> SEQ ID NO 5
<211> LENGTH: 20
<212> TYPE: DNA
<213> ORGANISM: Artificial Sequence
<220> FEATURE:
<223> OTHER INFORMATION: synthetic primer

<400> SEQUENCE: 5
gactggcatt ttgcatttgt                                              20

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
agacaagcaa aagctctttg                                              20

<210> SEQ ID NO 7
<211> LENGTH: 19
<212> TYPE: DNA
<213> ORGANISM: Artificial Sequence
<220> FEATURE:
<223> OTHER INFORMATION: synthetic primer

<400> SEQUENCE: 7
tccatctctg aatcaatgt                                               19

<210> SEQ ID NO 8
<211> LENGTH: 19
<212> TYPE: DNA
<213> ORGANISM: Artificial Sequence
<220> FEATURE:
```

-continued

<223> OTHER INFORMATION: synthetic primer

<400> SEQUENCE: 8
gcaatggaat gaaatgaca                                              19

<210> SEQ ID NO 9
<211> LENGTH: 24
<212> TYPE: DNA
<213> ORGANISM: Artificial Sequence
<220> FEATURE:
<223> OTHER INFORMATION: synthetic primer

<400> SEQUENCE: 9
gttttagggt attggtaatt tggt                                        24

<210> SEQ ID NO 10
<211> LENGTH: 21
<212> TYPE: DNA
<213> ORGANISM: Artificial Sequence
<220> FEATURE:
<223> OTHER INFORMATION: synthetic primer

<400> SEQUENCE: 10
gaccacccta ttccaccact a                                           21

<210> SEQ ID NO 11
<211> LENGTH: 22
<212> TYPE: DNA
<213> ORGANISM: Artificial Sequence
<220> FEATURE:
<223> OTHER INFORMATION: synthetic primer

<400> SEQUENCE: 11
caaactaata acaccccac ca                                           22

<210> SEQ ID NO 12
<211> LENGTH: 24
<212> TYPE: DNA
<213> ORGANISM: Artificial Sequence
<220> FEATURE:
<223> OTHER INFORMATION: synthetic primer

<400> SEQUENCE: 12
ggtaatttgg ttagaggatc gcgc                                        24

<210> SEQ ID NO 13
<211> LENGTH: 23
<212> TYPE: DNA
<213> ORGANISM: Artificial Sequence
<220> FEATURE:
<223> OTHER INFORMATION: synthetic primer

<400> SEQUENCE: 13
cgtcgtaaga attcggaggg gtg                                         23

<210> SEQ ID NO 14
<211> LENGTH: 28
<212> TYPE: DNA
<213> ORGANISM: Artificial Sequence
<220> FEATURE:
<223> OTHER INFORMATION: synthetic primer

<400> SEQUENCE: 14
tattggtaat ttggttagag gattgtgt                                    28

```
<210> SEQ ID NO 15
<211> LENGTH: 25
<212> TYPE: DNA
<213> ORGANISM: Artificial Sequence
<220> FEATURE:
<223> OTHER INFORMATION: synthetic primer

<400> SEQUENCE: 15
tgttgtaaga atttggaggg gtgtg                                           25

<210> SEQ ID NO 16
<211> LENGTH: 21
<212> TYPE: DNA
<213> ORGANISM: Artificial Sequence
<220> FEATURE:
<223> OTHER INFORMATION: synthetic primer

<400> SEQUENCE: 16
atagagccac actttgtctc a                                               21

<210> SEQ ID NO 17
<211> LENGTH: 21
<212> TYPE: DNA
<213> ORGANISM: Artificial Sequence
<220> FEATURE:
<223> OTHER INFORMATION: synthetic primer

<400> SEQUENCE: 17
tctttgagaa ccactgtctc c                                               21

<210> SEQ ID NO 18
<211> LENGTH: 25
<212> TYPE: DNA
<213> ORGANISM: Artificial Sequence
<220> FEATURE:
<223> OTHER INFORMATION: synthetic primer

<400> SEQUENCE: 18
cctatctcca tctatttatc tgtct                                           25

<210> SEQ ID NO 19
<211> LENGTH: 20
<212> TYPE: DNA
<213> ORGANISM: Artificial Sequence
<220> FEATURE:
<223> OTHER INFORMATION: synthetic primer

<400> SEQUENCE: 19
aatcagatcc ccttggaaag                                                 20

<210> SEQ ID NO 20
<211> LENGTH: 20
<212> TYPE: DNA
<213> ORGANISM: Artificial Sequence
<220> FEATURE:
<223> OTHER INFORMATION: synthetic primer

<400> SEQUENCE: 20
taccttcctt ccccactctt                                                 20

<210> SEQ ID NO 21
<211> LENGTH: 20
<212> TYPE: DNA
<213> ORGANISM: Artificial Sequence
<220> FEATURE:
<223> OTHER INFORMATION: synthetic primer
```

```
<400> SEQUENCE: 21
caaaccagaa gtgggagaga                                              20

<210> SEQ ID NO 22
<211> LENGTH: 24
<212> TYPE: DNA
<213> ORGANISM: Artificial Sequence
<220> FEATURE:
<223> OTHER INFORMATION: synthetic primer

<400> SEQUENCE: 22
agtacaaata cacacaaatg tctc                                         24

<210> SEQ ID NO 23
<211> LENGTH: 17
<212> TYPE: DNA
<213> ORGANISM: Artificial Sequence
<220> FEATURE:
<223> OTHER INFORMATION: synthetic primer

<400> SEQUENCE: 23
gcaaatcgtt cattgct                                                 17

<210> SEQ ID NO 24
<211> LENGTH: 20
<212> TYPE: DNA
<213> ORGANISM: Artificial Sequence
<220> FEATURE:
<223> OTHER INFORMATION: synthetic primer

<400> SEQUENCE: 24
cattttaggt ggacgtctgc                                              20

<210> SEQ ID NO 25
<211> LENGTH: 20
<212> TYPE: DNA
<213> ORGANISM: Artificial Sequence
<220> FEATURE:
<223> OTHER INFORMATION: synthetic primer

<400> SEQUENCE: 25
aaccaccatg tcacgtgtat                                              20

<210> SEQ ID NO 26
<211> LENGTH: 16
<212> TYPE: DNA
<213> ORGANISM: Artificial Sequence
<220> FEATURE:
<223> OTHER INFORMATION: synthetic primer

<400> SEQUENCE: 26
gtgcccttcc agagtt                                                  16

<210> SEQ ID NO 27
<211> LENGTH: 18
<212> TYPE: DNA
<213> ORGANISM: Artificial Sequence
<220> FEATURE:
<223> OTHER INFORMATION: synthetic primer

<400> SEQUENCE: 27
agtgaggcat ccactacc                                                18

<210> SEQ ID NO 28
<211> LENGTH: 21
```

<212> TYPE: DNA
<213> ORGANISM: Artificial Sequence
<220> FEATURE:
<223> OTHER INFORMATION: synthetic primer

<400> SEQUENCE: 28
catctttctt ttcctgttcc c                                              21

<210> SEQ ID NO 29
<211> LENGTH: 24
<212> TYPE: DNA
<213> ORGANISM: Artificial Sequence
<220> FEATURE:
<223> OTHER INFORMATION: synthetic primer

<400> SEQUENCE: 29
gataccatat tcaacatgaa gagg                                           24

<210> SEQ ID NO 30
<211> LENGTH: 21
<212> TYPE: DNA
<213> ORGANISM: Artificial Sequence
<220> FEATURE:
<223> OTHER INFORMATION: synthetic primer

<400> SEQUENCE: 30
ctcactcatg aacacagatg c                                              21

<210> SEQ ID NO 31
<211> LENGTH: 22
<212> TYPE: DNA
<213> ORGANISM: Artificial Sequence
<220> FEATURE:
<223> OTHER INFORMATION: synthetic primer

<400> SEQUENCE: 31
aacccatctt gtattcttgc ag                                             22

<210> SEQ ID NO 32
<211> LENGTH: 21
<212> TYPE: DNA
<213> ORGANISM: Artificial Sequence
<220> FEATURE:
<223> OTHER INFORMATION: synthetic primer

<400> SEQUENCE: 32
aacgttggac ctcaagccca t                                              21

<210> SEQ ID NO 33
<211> LENGTH: 21
<212> TYPE: DNA
<213> ORGANISM: Artificial Sequence
<220> FEATURE:
<223> OTHER INFORMATION: synthetic primer

<400> SEQUENCE: 33
agaatgccaa ggaagggtgc a                                              21

<210> SEQ ID NO 34
<211> LENGTH: 24
<212> TYPE: DNA
<213> ORGANISM: Artificial Sequence
<220> FEATURE:
<223> OTHER INFORMATION: synthetic primer

<400> SEQUENCE: 34
tctctggcta aacatgatat atgg 24

<210> SEQ ID NO 35
<211> LENGTH: 20
<212> TYPE: DNA
<213> ORGANISM: Artificial Sequence
<220> FEATURE:
<223> OTHER INFORMATION: synthetic primer

<400> SEQUENCE: 35
tgggatcctg tctcaaaaaa 20

<210> SEQ ID NO 36
<211> LENGTH: 22
<212> TYPE: DNA
<213> ORGANISM: Artificial Sequence
<220> FEATURE:
<223> OTHER INFORMATION: synthetic primer

<400> SEQUENCE: 36
acctcttact tgtgttcttg gg 22

<210> SEQ ID NO 37
<211> LENGTH: 20
<212> TYPE: DNA
<213> ORGANISM: Artificial Sequence
<220> FEATURE:
<223> OTHER INFORMATION: synthetic primer

<400> SEQUENCE: 37
tgaccaagcc agtattggat 20

<210> SEQ ID NO 38
<211> LENGTH: 20
<212> TYPE: DNA
<213> ORGANISM: Artificial Sequence
<220> FEATURE:
<223> OTHER INFORMATION: synthetic primer

<400> SEQUENCE: 38
ggttgctgcc aaagattaga 20

<210> SEQ ID NO 39
<211> LENGTH: 20
<212> TYPE: DNA
<213> ORGANISM: Artificial Sequence
<220> FEATURE:
<223> OTHER INFORMATION: synthetic primer

<400> SEQUENCE: 39
cactgtgatt tgctgttgga 20

<210> SEQ ID NO 40
<211> LENGTH: 20
<212> TYPE: DNA
<213> ORGANISM: Artificial Sequence
<220> FEATURE:
<223> OTHER INFORMATION: synthetic primer

<400> SEQUENCE: 40
accacatgag ccaattctgt 20

<210> SEQ ID NO 41
<211> LENGTH: 22
<212> TYPE: DNA
<213> ORGANISM: Artificial Sequence

```
<220> FEATURE:
<223> OTHER INFORMATION: synthetic primer

<400> SEQUENCE: 41
acccaattat ggtgttgtta cc                                              22

<210> SEQ ID NO 42
<211> LENGTH: 20
<212> TYPE: DNA
<213> ORGANISM: Artificial Sequence
<220> FEATURE:
<223> OTHER INFORMATION: synthetic primer

<400> SEQUENCE: 42
gttgtacagc cgaccaagat                                                 20

<210> SEQ ID NO 43
<211> LENGTH: 22
<212> TYPE: DNA
<213> ORGANISM: Artificial Sequence
<220> FEATURE:
<223> OTHER INFORMATION: synthetic primer

<400> SEQUENCE: 43
tacacattca gattatgtgg gg                                              22

<210> SEQ ID NO 44
<211> LENGTH: 20
<212> TYPE: DNA
<213> ORGANISM: Artificial Sequence
<220> FEATURE:
<223> OTHER INFORMATION: synthetic primer

<400> SEQUENCE: 44
gaagaaactt tccctcctgc                                                 20

<210> SEQ ID NO 45
<211> LENGTH: 20
<212> TYPE: DNA
<213> ORGANISM: Artificial Sequence
<220> FEATURE:
<223> OTHER INFORMATION: synthetic primer

<400> SEQUENCE: 45
tctccttgtc atccttctgc                                                 20

<210> SEQ ID NO 46
<211> LENGTH: 21
<212> TYPE: DNA
<213> ORGANISM: Artificial Sequence
<220> FEATURE:
<223> OTHER INFORMATION: synthetic primer

<400> SEQUENCE: 46
catctgaaat gctgacctgt t                                               21

<210> SEQ ID NO 47
<211> LENGTH: 21
<212> TYPE: DNA
<213> ORGANISM: Artificial Sequence
<220> FEATURE:
<223> OTHER INFORMATION: synthetic primer

<400> SEQUENCE: 47
agctgtcaga actaagtgct t                                               21
```

PROGNOSTIC METHODS FOR BREAST CANCER

This invention was supported in part by a grant from the National Institutes of Health NIH P50 CA-58207. The U.S. Government may have rights in this invention.

INTRODUCTION

1. Technical Field

The invention relates to methods of predicting the likelihood of occurrence or re-occurrence of certain cancers, which methods are useful in determining the degree of aggressive treatment indicated, by analyzing the status of a particular chromosomal region. The invention also relates to methods of identifying compounds useful for cancer therapy by evaluating their effect on the status of a particular chromosomal region.

2. Background

Breast cancer is one of the most common cancers and is the third leading cause of death from cancers in the United States with an annual incidence of about 182,000 new death cases and nearly 50,000 deaths. In the industrialized world, approximately one in eight women can expect to develop breast cancer in her lifetime. Although the mortality rate for breast cancer has remained relatively unchanged since 1930, recent data suggest that breast cancer mortality is beginning to decrease, probably as a result of an increase in the diagnosis of localized cancer and carcinoma in situ. For review, see, Marchant (1994) Contemporary Management of Breast Disease 11: Breast Cancer, in: *Obstetrics and Gynecology Clinics of North America* 21:555–560; and Colditz (1993) *Cancer Suppl.* 71:1480–1489.

Although the etiology of breast cancer has not been elucidated, it is hypothesized to evolve from normal epithelium through certain non-malignant proliferative diseases to carcinoma in situ (Stage 0), either ductal or lobule, to primary invasive cancer (Stages I–IV) and finally, to metastatic (Stages III–IV). At some point in the progression from normal tissue to malignancy, tumor initiation occurs. Tumor initiation and the early stages of progression, do not necessarily render a cell malignant. The cells may, in fact, appear histologically normal even after initiation. A method of detecting mammary cells that have undergone tumor initiation but that are not yet neoplastic would be very useful in determining the most effective course of disease treatment.

Several genetic markers have been associated with breast cancer. A particular mutation in one of these, BRCAI, has recently been found to be associated with a specific ethnic group, Ashkenazi Jews, which has a particularly high incidence of breast cancer. A number of other tumor markers are associated with breast cancer, such as myc, p53, erbB2, bek, and fig (Adnane et al. (1991) *Oncogene* 6:659–661). The erbB2 gene (also known as HER-2/neu) encodes a 185 kDa membrane growth factor homologous to the epidermal growth factor receptor. The erbB2 gene is amplified in 61 of 283 tumors (22%) tested in a recent survey (Adnane et al. (1991)).

Another type of genetic marker of cancer, particularly invasive breast cancer and hyperplasia, is loss of heterozygosity (LOH). For review, see O'Connell (1994) *Breast Cancer Res. Treat.* 32:5–12. Loss of heterozygosity presumably indicates a loss of a growth-regulating tumor suppressor gene in that region (Matsumoto et al. (2000) *Cancer Lett.* 152:63–69). In breast cancer, LOH has been shown to be present at a number of different alleles in tumor cells. A high incidence of LOH has been found at chromosome 11q23 in non-familial breast cancers in situ, invasive and metastatic tumor cells (Koreth et al. (1995). *J. Pathol.* 176:11–18; Tomlinson et al. (1995) *J. Clin. Pathol.* 48:424–428). LOH has been found on chromosome 11q13 in 67% of microdissected invasive breast cancer and in a subpopulation of the in situ carcinomas of the invasive breast cancer (Zhuang et al. (1995) *Cancer Res.* 55:467–471). LOH has been found on chromosome 16q in intracystic papillary carcinomas in breast cancer and is thought to be involved in acquisition of malignant phenotype (Tsuda et al. (1994) *Jpn. J. Cancer Res.* 85:992–996). LOH has also been detected on two separate regions on chromosome 3p in breast cancers—3p13–14 and 3p24–26 (Chen et al. (1994) *Cancer Res.* 54:3021 *J. Natl Cancer Inst.* 81:1815–1820).

In a few cases, the LOH identified in the cancer cells has also been found in morphologically normal tissue adjacent to the tumor. Siegfried et al. (*Proc. Am. Assoc. Cancer Res.* (1995) 36:545 Abstract 3247) described a particular LOH at 3p21.3 that was found in non-small cell lung carcinoma and in adjacent, normal tissue. Deng et al. (*Science* (1996) 274:2057; WO98/17828) have described LOH at 3p24 in normal and hyperplastic benign tissue adjacent to breast carcinoma tissue.

Although therapy for breast cancer was originally restricted to radical mastectomy, more conservative, breast-preserving, surgeries are now often available. In addition, a wide variety of adjuvant therapies are now available including hormonal, radiation and chemotherapeutics. For review, see Posner et al. (1995) *Int. Surg.* 79:43–47. The availability of less radical treatment regimens necessitates the development of methods of identifying patients who are likely to exhibit tumor recurrence. There is evidence that suggests that ipsilateral recurrences of tumors, post-lumpectomy, may result not only from persistent tumor cells, but also de novo from an extended 'field' of increased susceptibility. Molecular indicators that can reliably detect the presence of putative progenitor populations in the absence of histologically identifiable changes, would be an important clinical adjunct.

SUMMARY OF THE INVENTION

We have now correlated the LOH at 3p24 that was found to be present in morphologically normal breast cells associated with tumor cells, as well as in the tumor cells (Deng et al. 1996), with increased likelihood of disease progression, particularly tumor recurrence. Breast cancer patients who exhibited LOH at 3p24 in both breast tumor and associated morphologically normal cells were 3.5 times more likely to experience a tumor re-occurrence within 5 yrs than patients who did not display the LOH in associated morphologically normal cells. In addition, we have narrowed the most common region of deletion associated with the predictive LOH to the particular chromosomal locus 3p24.3. A number of genes have been identified at the 3p24.3 locus, including the thyroid hormone receptor β1 gene (TRβ1). We have now found that the presence of LOH at 3p24.3 in tumor and in morphologically normal cells associated with the tumor correlates with an increased methylation level of the TRβ1 gene on the remaining allele, resulting in decreased, or no, expression of TRβ1 in the cells.

Accordingly, the present invention provides a method for determining the likelihood of tumor re-occurrence in a patient, who has been previously diagnosed with a breast tumor, by analyzing a target cell sample from the patient for the presence of LOH at chromosomal locus 3p24.3. The diagnosed breast tumor may be a malignant tumor or may be benign.

The present invention additionally provides a method for determining the aggressiveness for post-surgical treatment for a breast cancer patient by analyzing a target cell sample from the patient for the presence of LOH at chromosomal locus 3p24.3.

In another aspect, the invention provides a method for identifying a patient as being at risk for breast cancer by analyzing a breast cell sample from the patient for the presence of LOH at chromosomal locus 3p24.3.

In another aspect, the present invention provides a method for determining the likelihood of tumor re-occurrence in a patient, who has been previously diagnosed with a breast tumor, by analyzing a target cell sample from the patient for the expression of the thyroid hormone receptor β1 (TRβ1) gene. In this method, the expression of the TRβ1 gene can be determined by analysis at the mRNA or the protein level, or by examining the methylation state of the gene.

In a further aspect, the present invention provides a method for determining the aggressiveness for post-surgical treatment for a breast cancer patient by analyzing a target cell sample from the patient for the expression of the thyroid hormone receptor β1 gene. In this method, the expression of the TRβ1 gene can be determined by analysis at the mRNA or the protein level, or by examining the methylation state of the gene.

In another aspect, the invention provides a method for identifying a patient as being at risk for breast cancer by analyzing a breast cell sample from the patient for the expression of the thyroid hormone receptor β1 gene. In this method, the expression of the TRβ1 gene can be determined by analysis at the mRNA or the protein level, or by examining the methylation state of the gene.

In a separate aspect, the present invention provides a method of screening for a test compound useful for the treatment of breast cancer by providing a cancer cell line that has a hypermethylated TRβ1 gene promoter, contacting the cells with the compound to be tested, and determining the expression level of the TRβ1 gene in the presence and the absence of the test compound. Certain breast cancer cells lines are particularly useful in this aspect of the invention.

DESCRIPTION OF SPECIFIC EMBODIMENTS

The present invention provides a method for making a prognosis about disease course in a human cancer patient. For the purposes of this invention, the term "prognosis" is intended to encompass predictions and likelihood analysis of disease progression, particularly tumor recurrence, metastatic spread and disease relapse. The prognostic methods of the invention are intended to be used clinically in making decisions concerning treatment modalities, including therapeutic intervention, diagnostic criteria such as disease staging, and disease monitoring and surveillance for metastasis or recurrence of neoplastic disease. In addition to the prognostic methods, the present invention provides a screening method for identifying candidate therapeutic compounds for treatment of cancer.

The present invention provides a method for determining the likelihood of tumor re-occurrence in a patient, who has been previously diagnosed with a breast tumor, by analyzing a target cell sample from the patient for the presence of LOH at chromosomal locus 3p24.3. The present invention additionally provides a method for determining the degree of aggressiveness indicated for post-surgical treatment for a cancer patient, particularly a breast cancer patient, by analyzing a target cell sample from the patient for the presence of LOH at chromosomal locus 3p24.3. The methods of the present invention are useful for prognosing and determining the course of treatment for a number of cancers including breast, prostate, head and neck cancers. The methods of the present invention are particularly useful for prognosing and determining the therapeutic course for breast cancers, particularly at early stages.

The present invention provides a method for determining the likelihood of tumor re-occurrence in a patient previously diagnosed with a breast tumor comprising: (1) providing a target cell sample from the patient; (2) analyzing the target cell sample for loss of heterozygosity at chromosomal locus 3p24.3; and (3) classifying samples having LOH at chromosomal locus 3p24.3 as positive, wherein a positive sample indicates a greater likelihood of tumor re-occurrence. Patients whose target cell samples are classified as positive will typically have at least a two-fold, and possibly as much as a three-fold or three and a half-fold, higher risk of tumor re-occurrence than those patients whose target cell samples are not classified as positive. The present invention also provides a method of determining post-surgical treatment for a breast cancer patient comprising: (1) providing a target cell sample from the patient, (2) analyzing the target cell sample for loss of heterozygosity at chromosomal locus 3p24.3 and (3) classifying samples having LOH at chromosomal locus 3p24.3 as positive, wherein a positive sample is an indicator that more aggressive post-surgical treatment is indicated. For patients whose target cell samples are classified as positive, more aggressive treatment, such as additional surgical intervention or radiation or chemotherapy, should be considered.

For carrying out the methods of the invention for determining the likelihood of tumor re-occurrence and for determining post-surgical treatment, the target cell sample will typically be a sample of morphologically normal cells associated with the cancer cells or tumor. By "morphologically normal" is meant those cells that appear normal by assessment of those microscopic characteristics conventionally used by pathologists to distinguish malignant or hyperplastic cells from non-hyperplastic, non-malignant cells. By "associated with the tumor" is meant those cells that are in close physical proximity to the tumor or cancer cells and are generally excised in the same tissue block with the tumor. These associated cells will typically appear in the same field, when viewed in a microscopic sample, as the tumor or cancer cells. Target cell samples will typically be obtained from the morphologically normal cells that are excised with the cancer during the surgical procedure. In some cases, the target cell sample can also be benign hyperplastic tissue. In the case of a benign biopsy, the patient has no malignant tumor, but the biopsy tissue may harbor morphologically normal epithelium. Both the benign tumor cells and the associated morphologically normal cells are suitable as target cell samples for the methods of the present invention. For methods relating to breast tumors or breast cancers, a convenient target cell sample can be selected from the morphologically normal terminal ductal lobular units (TDLU) associated with the carcinoma. Target cells samples may be selected from cells that are more removed from the site of the tumor, however, information obtained from such cells may have less predictive value than that obtained from cells associated with the tumor or cancer cells.

The above methods are most effectively carried out in those cases in which the tumor or cancer cells exhibit LOH at 3p24.3. If convenient to the analysis, an additional step of analyzing the tumor or cancer cells for LOH at 3p24.3 may be carried out either before, after or simultaneously with the LOH analysis for the target cell sample.

The present invention also provides a method of identifying a patient as being at risk for breast cancer, said method comprising: (1) obtaining a breast tissue cell sample from said patient; (2) analyzing the breast tissue cell sample for loss of heterozygosity (LOH) at chromosomal locus 3p24.3; and (3) classifying patients whose breast tissue cell sample exhibit LOH at chromosomal locus 3p24.3 as at risk of breast cancer. By "at risk of breast cancer" is intended that the patient has a higher probability of developing breast cancer, including carcinoma in situ, primary invasive cancer, and metastatic cancer, than the general population. The increased risk would suggest a more careful and/or more frequent monitoring for other early indicators of breast cancer.

For this method, the breast cell sample may be any conveniently obtained sample of breast cells, including the target cell samples described above. Additionally, for this method the breast cell sample can be a non-invasively obtained breast cell sample; for example, the breast cell sample can be a nipple aspirate or ductal lavage sample. Methods for obtaining such samples are known in the art and used in the clinical setting (Love and Barsky (1996) Lancet 348: 997; Sauter et al. Br. J. Cancer 76:494; Phillips et al. Breast Cancer Res. Treat. (2000) 61:139). The breast cell sample can conveniently be a breast tissue biopsy sample.

Techniques for analyzing the loss of heterozygosity at any particular heterozygous locus are well known. See, for example, Deng et al. Cancer Res. 1994 54:499; Matsumoto et al. Genes, Chromosomes & Cancer 1997 20:268. The loss of heterozygosity at chromosomal locus 3p24.3 may be analyzed by any of these well known techniques or as described herein. In the typical case, the target cells to be analyzed will be substantially isolated from other cell populations, particularly from any cancer cells. Chromosomal DNA may be isolated from the target cells by any of a number of techniques that art well known in the art. In some cases, the subsequent analysis of LOH will not require that the DNA be completely or even substantially removed from other cell components. Typically, the polymorphic regions of the chromosomes to be analyzed are amplified by PCR using appropriate primers. Many polymorphic markers for chromosome 3 are well known and can be found at the web site for the National Center for Biotechnology Information of the National Library of Medicine of the National Institutes of Health. Primers that are particularly useful for amplifying the 3p24.3 locus include those listed in Table 2. The amplified regions from each heterozygous allele will differ in some detectable property, for example, size or restriction sites, such that two distinctive patterns are produced from heterozygous loci. When a deletion of one of the alleles occurs, only one of the patterns can be detected, hence there is a "loss of heterozygosity" (LOH) in that locus. In most cases experimentally, the LOH will not appear as a complete loss of the pattern from the deleted allele (because the analysis will be carried out on a population of cells, not all of whose chromosomes necessarily exhibit an allelic deletion), but as a decrease in the intensity of the signal from one allele. The intensities of the allelic signals for the target cell sample or the breast cell sample can be measured against the allelic signals from a control cell sample for a comparison. The control cell sample for LOH analysis will be a non-malignant cell sample from the same individual from whom the target cell sample is obtained. The control cell sample will generally be taken from an organ that is unaffected by the cancer. For example, in the case of breast cancer, typical control cell samples can be skin, lymph node or blood cells samples. One of ordinary skill in the art is competent to select other appropriate control cell samples for the particular application.

Identification of an LOH at 3p24.3 in the morphologically normal cells associated with a tumor or cancer cells has several important clinical implications. For example, application of methods to detect these high-risk lesions as described herein could significantly decrease the risk of tumor recurrence by ensuring that the entire tissue region exhibiting the 3p24.3 LOH is surgically removed. In addition, or alternatively, radiation therapy can be adjusted to ensure the elimination of cells with 3p24.3 LOH at the edge of the field of radiation. Similarly, prior knowledge of the presence of allelic loss in morphologically normal TDLU associated with carcinoma would justify inclusion of these patients in chemoprevention trials.

The present inventors have correlated LOH at chromosomal locus 3p24.3 in morphologically normal cells with an increased risk for the development of cancer in those cells. Additionally, they have found that the LOH at 3p24.3 is correlated with a decrease in expression of the thyroid hormone receptor β1 gene in these cells. This decrease in expression is not due entirely to the deletion of the gene as one copy of the gene is still present on the remaining allele. Rather, the decrease in expression can be attributed to an increase in methylation of the TRβ1 promoter. Therefore, analysis of the methylation state of the chromosome in the region of the TRβ1 promoter or analysis of the expression of the TRβ1 gene, can provide a similar kind of predictive information as analysis of the LOH at 3p24.3.

Accordingly, the present invention also provides a method for determining the likelihood of tumor re-occurrence in a patient previously diagnosed with a breast tumor comprising: (1) providing a target cell sample from said patient, (2) analyzing the target cell sample for the level of expression of thyroid hormone receptor β1 gene compared to a control cell sample; (3) classifying a target cell sample having a lower level of expression of thyroid hormone receptor β1 compared to the control cell sample as positive, wherein a positive sample indicates a greater likelihood of tumor re-occurrence.

The target cell sample for this method will be similar to that described above for the analysis of LOH and will typically be a sample of morphologically normal cells taken from the tissue associated with the cancer cells or tumor. The target cells may also include benign hyperplastic cells. Because of the greater amount of cell sample typically required for analysis of the TRβ1 gene expression, the target cell sample will typically include a greater area of tissue peripheral to the tumor or breast cancer.

The analysis of the expression of the TRβ1 gene can be carried out by any of several techniques that are well known in the art. The expression of the gene can be measured by the amount of mRNA present or the rate of mRNA synthesis, or by the amount or activity of protein present. In addition, an indirect measure of the expression of the gene can be determined by examining the methylation level of the gene, particularly in the promoter region. In general, the greater the amount of methylation, particularly at the region around the promoter, the lower the expression of the gene.

Techniques for analysis of the level of any particular transcript in a cell are well known in the art and include, for example, Northern blot analysis and RT-PCR (See, for example, Sambrook et al. Molecular Cloning: A Laboratory Manual, $2^{nd}$ Ed. Cold Spring Harbor Laboratories Press 1989; Mocharla et al. Gene 1990 93:271). For analysis of mRNA transcript levels for the TRβ1 gene, a particularly useful technique is RT-PCR. Primers that are useful in this regard include TRβ-F and TRβ-R. Other useful primers and probes may be designed based on the sequence of the TRβ1 gene and mRNA (Weinberger et al. Nature (1986) 324:641; Human Genome Project Working Draft by methods that are well known. Analysis of the level of the TRβ1 protein may be carried out by any convenient method; for example, Western blot analysis and ELISA assay (Sambrook et al. 1989). Immunoassays using anti-TRβ1 antibodies, for example, monoclonal antibody J51, are particularly useful in the method of the present invention. Analysis of the expression of the TRβ1 gene in the target cells will include the comparison to TRβ1 gene expression in a control cell sample. One of ordinary skill in the art is competent to select the appropriate control cell sample. The control cell sample will generally include cells of the same type from the same tissue as the target cells but will be from a cancer free individual or from a cancer free region of the patient. Standard control cell samples can be developed for use with different target cell samples. Moreover, standard values for TRβ1 expression levels can be developed from the control cell samples, for both mRNA and protein analysis, such that actual measurement of the expression in the control cell sample need not be carried out with each analysis, but rather the target cell samples can be compared to a standard value for protein or mRNA developed from the control cell samples.

Techniques for analyzing the methylation state of chromosomal DNA are well known and include, for example, methylation specific PCR (MSP) and combined bisulfite restriction analysis (COBRA). Typically, the analysis is carried out by either method. Primers that are particularly useful in the present method for determining the methylation state of the TRβ1 gene include CVT3F, CVT4R, M1F, M1R, U1F and U1R and CVT3R, but other primers can be designed based on the known sequence of the gene.

The present inventors have discovered that the LOH at 3p24.3 that is seen in some breast tumors and in the associated morphologically normal breast cells correlates with an increased methylation of the remaining allele at 3p24.3, particularly at the TRβ1 gene. They have discovered that a number of previously described breast cancer cell lines exhibit both genetic deletion at 3p24.3 and hypermethylation of the remaining TRβ1 promoter. These cancer cell lines do not express TRβ1, or express it a very low level compared to non-cancerous breast cell lines. Exposure of the breast cancer cell lines to a demethylating agent however results in a higher level of TRβ1 expression in the cancer cells lines. This suggests that these breast cancer cell lines and other cancer cell lines that exhibit a hypermethylated TRβ1 gene promoter would be useful in a screening assay to identify compounds that are useful as a therapeutic for cancers, particularly for cancers exhibiting the LOH at 3p24.3. Breast cancer cells lines that are particularly useful in the screening method of the present invention include the well know cell lines MDA435, SKBR3 and DU4475, preferably MDA435 and SKBR3. These cell lines are available from the American Type Culture Collection, Manassas, Va., USA. Other useful cancer cell lines can be readily identified by examining the level of methylation and/or expression of the TRβ1 gene and by analyzing for LOH at 3p24.3 as described herein.

The screening assay of the present invention can be conveniently carried out by contacting the appropriate cancer cell line with a test compound, determining the level of thyroid hormone receptor β1 expression in the cells in the presence of the test compound and comparing that to the level of thyroid hormone receptor β1 expression in the cells in the absence of the test compound. Those test compounds that produce an increase in the expression level of the TRβ1 gene are selected as candidate therapeutic compounds.

The following examples are provided by was of illustration and are not intended to limit in any way the claimed invention.

EXAMPLES

Example 1

Correlation of Tumor Re-Occurrence in Breast Cancer Patients with the Presence of LOH at 3p24.3

ACQUISITION OF ARCHIVAL TISSUE SAMPLES AND MICRODISSECTION

Non-malignant lymph node or skin tissue was obtained from 98 cases of infiltrating ductal carcinoma from Stage I and II patients treated with breast conserving surgery at the California Pacific Medical Center, and the University of California, San Francisco Medical Center, under IRB approved guidelines. All cases were diagnosed during 1986 to 1993. The cases initially selected included those known to have local and distant recurrences during follow up, and those with no recurrence for a minimum of 5 years of follow up. DNA was isolated and analyzed for the presence of heterozygosity at loci on chromosome 3p.

Analysis of allelic loss was performed in 64 informative cases. First, non-malignant skin or lymph node and tumor DNA was compared. Those tumors, which displayed LOH, were further tested for the presence of LOH in morphologically normal TDLU adjacent to tumor. Serial 5 μm sections of tumor tissue were cut from paraffin-embedded blocks. Histologic details were examined in one hematoxylin-eosin stained and mounted section at 200× magnification. Subsequent serial sections were used for microdissection at 20× magnification. To obtain a sufficient amount of DNA, the same lobule or group of tumor cells was microdissected and pooled from 2–5 sequential sections. The criteria for selection of normal TDLU were the presence of several acini displaying prominent lumens. Each acinus was confirmed to consist of a single continuous myoepithelial or basal layer surrounding a single layer of luminal epithelium in which uniformly small nuclei with evenly distributed chromatin were present (as reviewed and ascertained by two pathologists). Molecular analyses were blinded to patient outcome until completion of allelic ratio determination.

STATISTICAL ANALYSIS

Only patients treated with lumpectomy and radiation who displayed 3pLOH in the tumor were selected for statistical analyses. Clinical data analyzed included: patient status (alive, with local or distant recurrence, or no evidence of disease), age, lymph node positivity, tumor grade, tumor size, tumor margins (negative or positive), chemotherapy (yes or no) and hormonal therapy (yes or no). Information on patient follow up was based on chart review facilitated by the UCSF Breast Oncology Program Epidemiology Core.

LOH ANALYSIS

The microdissected material was incubated in lysis buffer (10 mM Tris-HCl, 1 mM EDTA, 1% Tween-20, 400 mg/ml proteinase K) at a concentration of 50 cells/ml at 50° C. until the sample was clear. A template volume containing the equivalent of 50 cells was amplified at loci containing RFLP or microsatellite repeats using the Polymerase Chain Reaction (PCR). The particular loci amplified are listed in Table 1. All reactions were carried out in parallel duplicates of a 10 ml PCR mix with a total of 40 PCR cycles. The sequences of primers used to amplify each of the loci are listed in Table 2.

To ensure allelic representation, and to eliminate technical artifacts often associated with LOH analysis, the following steps were included: a) the number of cells were counted prior to microdissection and solubilized in a standard volume/cell ratio and b) intensity of PCR-amplified alleles was compared both within multiple runs and between various samples of the same specimen. The mean variation in allelic ratio between duplicate reactions within a given sample at the same locus was 5% (range 0.3% to 11.8%). LOH was recorded if 1) a >30% difference was observed between the allelic ratio of control and test sample and 2) <5% difference in the ratio between duplicate reactions within a given sample.

Results

We assessed LOH in 64 informative cases of conservatively treated early stage primary invasive breast carcinoma and adjacent normal TDLUs for LOH at chromosome 3p11–26. Stage I and II tumors were selected in order to reduce the possibility that normal TDLUs with LOH would be overgrown by aggressive malignant populations. LOH involving at least one locus within 3p11–26 was present in 75% (48 out of 64) of the tumors. LOH was also found to occur in morphologically normal TDLU associated with the tumor cells in over one-fourth (13 out of 48) of these cases. In all samples (13/13) showing 3pLOHn, malignant cells and normal TDLUs displayed loss of the same allele at all loci, indicating a significant probability (p=<0.001) that the tumors had originated within LOH-harboring TDLUs. "3pLOHn" refers to cases where the LOH is at 3p24.3 in the tumor cells and in the associated morphologically normal cells. Detailed LOH analysis results at 15 polymorphic loci for the 48 patient samples in which some LOH was found within 3p11–26 is shown in Table 1. The double plus (++) indicates LOH found in both tumor cells and the normal adjacent TDLUs, the single plus (+) indicates the LOH found in tumor only, the minus(−) indicates that no LOH was found, NI indicates that the sample was not informative at the locus, a blank indicates that the sample was not tested at the locus.

We mapped the region of LOH within 3p11–26 at 15 polymorphic loci in 13 matched pairs of primary tumor and individually microdissected morphologically normal adjacent TDLU in order to define the region of common LOH as narrowly as possible The 3pLOH analysis of morphologically normal TDLUs was important since it ensured that the region defined was associated with early tumorigenesis rather than with events that occurred in later stages of tumor progression and/or those that resulted from downstream genomic instability. The validity of this approach is confirmed by the fact that the regions of LOH were generally larger in the tumors than in the normal TDLUs. Specifically, 11/13 morphologically normal adjacent TDLU displayed loss at $\leq 2$ sequential loci, while almost one-third (15/48) of the tumor samples showed loss of $\geq 3$ sequential loci. It is unlikely that microdissected normal TDLU contain microscopically undetected invasive tumor cells. This reasoning is based on the fact that detection of LOH would require $\geq 70\%$ of the cell mixture to be occult tumor cells. The EABMD/H locus (Ganly and Rabbitts, Nucleic Acids Res. (1991) 19:3760–61) within 3p24.3 was the most common region of LOH, occurring in 7/7 informative normal/tumor pairs (p=0.11).

We tested the association of 3pLOHn with tumor recurrence in 33/48 cases from the original set of patients, all of whom displayed 3pLOH in the tumor. This approach was taken to exclude the contribution of LOH in the malignant component of the tumor towards an unusually aggressive phenotype. The data were analyzed in two ways.

In the first analysis, recurrence incidence rates based on clinical outcome (at 11–108 months after primary diagnosis) were compared for patients with and without 3pLOHn (Table 3). Since the patient set was initially seeded with recurrent cases, the overall rate of recurrence in this study is not representative of early stage disease. Eleven patients who displayed 3pLOHn were matched 1:2, for age, stage, and nodal status with cases that did not display 3pLOHn. Ten of 11 patients with 3pLOHn developed a recurrent tumor. The total follow up period for this group was 627 months leading to a recurrence rate of 0.0159 recurrences per month of follow-up. This was compared to recurrences observed in 7 of 22 matched controls without 3pLOHn. Total follow-up period for the controls was 1592 months and the estimated recurrence rate was 0.0044 recurrences per month of follow-up. The difference in the incidence rate between the 2 subsets was 0.0116 (95% CI 0.0011 to 0.0220) and the incidence rate ratio was 3.63 (95% CI 1.25 to 11.23). These differences are statistically significant at p=0.0100 (two-sided) based on comparison of binomial proportions (Rothman K J, editor, Modem Epidemiology. Boston: Little Brown and Company, 1986).

In the second analysis, we compared cases that recurred within 5 yr. of the primary tumor diagnosis with those that did not recur within 5 yr., matched 1:2 for age, stage, and nodal status (Table 4). Eleven patients recurred within 5 yr. and 22 did not. The incidence rate of 3pLOHn was 7/11 in patients with recurrences vs. 4/22 in patients without recurrence. The relative risk of recurrence for 3pLOHn was 3.50 (95% CI 1.3 to 9.4; p=0.014). Thus, both analyses demonstrated a strong association between 3pLOHn and increased risk of recurrence. Differences in tumor grade, tumor margins, and administration of chemotherapy or hormone therapy between the patients with 3pLOHn, and those without, were not sufficient to explain the difference in incidence rates of recurrence identified by the presence of 3pLOHn.

Recurrences observed in this study could have been caused by outgrowth of residual tumor cells or by development of a new primary tumor. The increased risk of recurrence associated with 3pLOHn suggests that it is not due to regrowth of persistent tumor cells. Instead, the data support the assumption that the presence of 3pLOHn predisposes the cells harboring this lesion to de novo development of a new primary tumor. Two additional observations support this interpretation. First, recurrences in patients with 3pLOHn are more frequently local than in those without 3pLOHn. Specifically, the incidence of local recurrence was 5.08-fold higher for patients with 3pLOHn than for those without (95% CI 1.08 to 31.38; two sided p=0.022), whereas the rate for contralateral and distant recurrence between the 2 groups was not significantly different (two-sided p=0.21). Secondly, the time to local recurrence was significantly longer for those with 3pLOHn than for those without (p=0.020 based on Wilcoxon rank sum test, two-sided). These findings are consistent with a model in which tumors are likely to take longer to develop de novo from predisposed TDLU than from residual tumor cells.

Discussion

The increased risk associated with the presence of 3pLOHn appears to be due to a tumor suppressor gene in the region of LOH, which contributes to tumorigenesis when inactivated by a second event. Several genes on 3p have been implicated as tumor suppressor genes in breast and other cancers. These include FHIT at 3p14.2 (Negrini M, et al. Cancer Res 1996;56:3173–3179; Campiglio M, et al. Cancer Res 1999;59:3866–3869) and VHL at 3p25 (Latif F. et al. Science 1993;260:1317–1320). However, both of these candidates are outside the region of common deletion at 3p24.3 defined in this study. Thus, it is likely that neither of these genes is the suppressor gene involved in 3pLOHn related risk. Candidate genes in the region of most common LOH in morphologically normal TDLU include hTRβ and retinoic acid receptor β2 (RARβ2). Although loci at 3p have been evaluated as markers of tumor aggressiveness in breast cancer (Matsumoto et al. Cancer Lett 2000 152:63), a role in early tumorigenesis has not been demonstrated. Similarly, at other chromosomal loci, a search for correlations between LOH in proliferative benign disease and subsequent risk of malignancy suggests that not all LOH sites are clinically meaningful (Kasani et al., Am J Pathol 1997 150:1925).

The most likely explanantion for the increased risk associated with 3pLOHn is that 3pLOH in morphologically normal TDLUs results from a pre-pubertal genetic insult to aprogenitor cell that is subsequently propagated in one or more branches of the mammary tree during breast development. The extent of breast tissue harboring LOH will depend on when during development the LOH occurs and is likely to vary among patients.

Example 2

Expression Analysis of the Thyroid Hormone Receptor β1

Thyroid hormone receptors are ligand-mediated transcription factors, which form complexes with other nuclear receptors and multiple effector proteins to orchestrate cell differentiation during growth and development (Horlein et al. Nature (1995) 377:397; Chen and Evans Nature (1995) 377:454; Burris et al. Proc Natl Acad Sci USA (1995) 92:9525). Loss of gene function associated with v erb A, a mutated variant of thyroid hormone receptor α (Sap et al. Nature (1986) 324:635; Weinberger et al. Nature (1986) 324:641), arrests normal differentiation of avian erythroblast progenitors resulting in virally induced leukemic transformation (Kahn et al. Cell (1986) 45:349; Zenke et al. Cell (1990) 61:1035). Deletions encompassing TRβ are suspected to play a role in the genesis of small cell lung cancer (Dobrovic et al. Cancer Res (1988) 48:682). The experiments described herein show that, in conjunction with LOH, epigenetic changes in the promoter region of the TRβ1 gene lead to complete inactivation of the gene in Stage I and II invasive breast tumors.

The region of most common LOH in the experiments described in Example I include the region of the TRβ1 gene. Therefore, we evaluated TRβ1 gene expression in breast cancer cell lines by RT-PCR, using primers encompassing exons 4–7. The primers used for RT-PCR of the TRβ1 transcript were TRβ-F 5' GAACAGTCGTCGCCACATCTC 3' (forward) (SEQ ID NO:1) and TRβ-R 5' TGAGCTCCCATTCCTCGTC 3' (reverse) (SEQ ID NO:2). Presence of a TRβ1 transcript was indicated by the presence of a 500 bp RT-PCR product using template mRNA isolated from non-cancerous or breast cancer cell lines. As a control, corresponding GAPDH transcript levels for each sample was measured within the same PCR reaction mixture by amplifying a 250 bp fragment using the following primers 5' TGATGACATCAAGAAGGTGGTGAA 3' (forward) (SEQ ID NO:3) and 5' TCCTTGGAGGCCATGTGGGCCAT 3' (reverse) (SEQ ID NO:4). Transcript levels in normal breast organoids prior to cell culture and in cultures of the same specimen at passage 2 showed close similarity. Breast cancer cell lines displayed a range of TRβ1 gene expression. Fluorescent in situ hybridization (FISH) analysis was carried out on the cells to determine the copy number of the TRβ1 gene. FISH data is reported as the percentage of cells in which TRβ1 copy number was fewer than the centromeric signal for chromosome 3. The breast cancer cell lines that were used in this study include DU4475, MDA435, SKBR3, MCF7, BT20, MDA157, MDA231, BT474, CAMA1 and T47D. All of these cell lines are available from American Type Culture Collection, Manassas, Va. The results of the RT-PCR and FISH analysis are summarized in Table 6.

TRβ1 transcript levels below those found in non-cancerous breast epithelial cultures from a non-malignant reduction mammoplasty specimen were observed in 3/10 breast cancer cell lines examined. Transcripts for TRβ1 were not detectable in cell lines DU4475, MDA 435 and SKBR3 although FISH signals for the TRβ1 gene using a TRβ1 specific genomic probe for signal enumeration in interphase nuclei were detectable in the two latter lines examined. The DU4475 cell line was not examined for TRβ1 gene copy number. Homozygous deletions of TRβ1 gene were not detected in any breast cancer cell line. Similarly, in primary tumors, deletions were limited to loss of a single allele as determined by LOH analysis (Example 1). Moreover, in cDNA made from mRNA isolated from cell lines and primary tumors (12 cases) no mutations were detected by SSCP analysis within exons 9 and 10. SSCP analysis was carried out using the following primers for exon 9: Ex9F GACTGGCATTTTGCATTTGT (SEQ ID NO:5) and Ex9R AGACAAGCAAAAGCTCTTTG (SEQ ID NO:6); and for exon 10: Ex10F TCCATCTCTGAATCAATGT (SEQ ID NO:7) and Ex10R GCAATGGAATGAAATGACA (SEQ ID NO:8). The region encodes the ligand binding region, a common site of TRβ1 germ line mutations in syndromes unrelated to cancer (Weiss et al. J Clin Invest 1993 91:2408).

The abundance of CpG islands in the 5' region of the gene led us to examine the role of promoter hypermethylation in TRβ1 gene silencing using methylation specific PCR (MSP) (Herman et al. Proc. Natl Acad Sci USA 1996 93:9821) and combined bisulfite restriction analysis (COBRA) (Xiong et al. Nucleic Acids Res 1997 25:2532). The CVT3F/CVT4R primer set was used to amplify sodium bisulfite converted genomic DNA in the first round of a nested PCR. In the second round of PCR, primers M1F, M1R, U1F and U1R were used for MSP analysis, while CVT3F/CVT3R were used for COBRA. Taq I restriction was used to distinguish between methylated and unmethylated DNA. Primer sequences were as follows:

```
COBRA
CVT3F:  GTTTTAGGGTATTGGTAATTTGGT      (SEQ ID NO:9)

CVT4R:  GACCACCCTATTCCACCACTA         (SEQ ID NO:10)

CVT3R:  CAAACTAATAACACCCCCACCA        (SEQ ID NO:11)

MSP
M1F:    GGTAATTTGGTTAGAGGATCGCGC      (SEQ ID NO:12)
```

```
            -continued
M1R:   CGTCGTAAGAATTCGGAGGGGTG        (SEQ ID NO:13)

U1F:   TATTGGTAATTTGGTTAGAGGATTGTGT   (SEQ ID NO:14)

U1R:   TGTTGTAAGAATTTGGAGGGGTGTG      (SEQ ID NO:15)
```

The results of the MSP and COBRA analyses are summarized in Table 6.

While DNA sequence analysis confirmed the unmethylated status of the gene in non-cancerous breast epithelial cells isolated from reduction mammoplasty samples, breast cancer cells, such as MDA435, displayed methylation of 27/27 potential CpG sites in a 325 bp region spanning the first exon-intron junction within the CpG island of the gene promoter. Among the cell lines (with the exception of BT474), reduction in gene copy number and hypermethylation were concordant.

Cell lines were treated with 1 mM 5-aza-2'-deoxycytidine for 5 days and mRNA was again isolated. 5-aza-deoxycytidine treatment of MDA435 and SKBR3 restored TRβ1 transcript expression in both cases demonstrating that silencing of the gene by methylation at the DNA level is partially reversible (Table 6). Concurrent analyses of the same cells for another methylated gene in the 3p24 region, RARβ, showed discordant hypermethylation of the two genes, suggesting that these may be alternate or independent events in tumor progression. Transcript levels of RARβ were unaltered by treatment with 5-aza-deoxycytidine alone as previously described (Sirchia SM, et al. Oncogene (2000) 19:1556; Widschwendter M, et al. J Natl Cancer Inst (2000) 92:826).

In addition to breast cancer cell lines, DNA isolated from 11 matched cases of primary breast tumors and tissue peripheral to carcinoma was evaluated for TRβ1 promoter hypermethylation in a sensitive, two-stage, nested PCR strategy. The results demonstrated that methylation in tumor cells was common. Considerable intra and intertumor variability was observed in the degree of methylation. Methylation was not restricted to the tumor cells but was also found to occur in DNA isolated from non-malignant tissue peripheral to carcinoma. Samples which displayed TRβ1 gene methylation in the tumor alone were predominantly from younger (<50 years) patients. Age-related methylation of other known genes in normal appearing tissue associated with cancer has been attributed to "field defects" (Issa et al. 1994 Nat. Genet. 7:536). To our knowledge, this is the first report demonstrating TRβ1 promoter methylation in cancerous and non-malignant peripheral tissue.

Next, we assessed the concordance of promoter methylation, LOH, and expression patterns of nuclear TRβ1 protein in cryosections of primary breast tumors. Immunohistochemical detection of TRβ1 gene product (using monoclonal antibody, J51 purchased from Santa Cruz Biotech. Inc) demonstrated a range of expression from homogeneously positive to undetectable levels in tumor cells. Table 5 summarizes the data. In 3 cases, marked heterogeneity was observed with nuclear positive and negative tumor cells within a single microscopic field. These observations suggest that TRβ1 methylation is a progressive phenomenon.

It has been shown previously that the addition of the ligand, thyroid hormone, to prostate and breast epithelial cultures inhibits cell proliferation (Martinez et al. Cancer Chemother Pharmacol. 2000 45:93). It appears that to evade the constraints of regulated cell proliferation, elimination of classical gatekeeper and caretaker genes (Kinzler K W, Vogelstein B. Science (1998) 280:1036) during the early stages of cancer progression, may be as critical as loss of those that induce terminal differentiation. For example, a shift in the balance of other transcription factor complexes, such as, myc/max/mad is also known to impair differentiation (Foley et al. Biochim Biophys Acta (1999) 1423:M37). The experiments disclosed herein of an increased risk of tumor recurrence associated with the presence of deletions encompassing the TRβ1 region in morphologically normal TDLU within the breast tumors, suggests that early reduction in TRβ1 gene copy number may confer a subsequent selective advantage for escaping differentiation cues. Although specific genetic targets of TRβ1 inactivation presently remain unknown, knowledge of mechanisms that inactivate this ligand-induced master switch is important in designing appropriate strategies for gene-based cancer intervention.

TABLE 1

LOH Analysis At Polymorphic Loci For Breast Cancer Cells

| Locus | Case # | | | | | | | | | | | | | | | | | | | | | |
|---|---|---|---|---|---|---|---|---|---|---|---|---|---|---|---|---|---|---|---|---|---|---|
| | 4 | 5 | 8 | 9 | 10 | 12 | 13 | 15 | 16 | 17 | 18 | 19 | 20 | 21 | 22 | 25 | 27 | 28 | 30 | 31 | 32 | 33 | 34 |
| D3S2397 | | | | | − | NI | | | | | | | | | | | | | | | | | |
| 71G12 | | | | | NI | NI | | − | NI | | | | | NI | ++ | NI | NI | | | | | NI | |
| D3S2405 | − | + | NI | | | | − | ++ | NI | | | | | NI | | + | | | | | | + | + |
| D3S1597 | | | | | | | | | | | | | | | | | | | | | | | NI |
| D3S2414 | − | + | − | + | ++ | − | − | ++ | − | + | + | ++ | + | ++ | | NI | ++ | | + | − | | + | + |
| D3S1244 | | | | | | | | | | | | | | | | | | | | | | | + |
| D3S3038 | − | | NI | | | | | + | | ++ | | | | NI | | NI | NI | | | | | | − |
| D3S1255 | | | | | | | | | | | | | | | | | | | | | | | |
| EABMD/H | ++ | + | − | NI | NI | ++ | NI | ++ | NI | NI | | NI | NI | NI | ++ | NI | NI | + | NI | − | + | + | NI |
| D3S2423 | NI | + | + | + | | | + | NI | + | NI | NI | − | | NI | NI | ++ | ++ | | NI | + | | | NI |
| D3S2396 | | | | | | NI | | | NI | NI | | | | | + | ++ | + | | | | | + | |
| D3S1768 | | | | | | NI | | | NI | | | | | | NI | NI | + | | | | | + | − |

TABLE 1-continued

LOH Analysis At Polymorphic Loci For Breast Cancer Cells

| Locus | | | | | | | | | | | | | | | | |
|---|---|---|---|---|---|---|---|---|---|---|---|---|---|---|---|---|
| D3S1766 | | + | + | | NI | NI | | | NI | NI | + | | | | − | |
| 2C06 | | | | | | | | | NI | ++ | + | | | | | NI |
| D3S2438 | | | | | | | | | NI | NI | NI | | | | | |

| | Case # | | | | | | | | | | | | | | | | | | | | | | | | |
|---|---|---|---|---|---|---|---|---|---|---|---|---|---|---|---|---|---|---|---|---|---|---|---|---|---|
| Locus | 35 | 38 | 39 | 40 | 41 | 42 | 43 | 44 | 45 | 46 | 47 | 48 | 49 | 50 | 52 | 53 | 54 | 55 | 56 | 57 | 58 | 59 | 61 | 63 | 64 |
| D3S2397 | NI | NI | | NI | | | | | | | | NI | | NI | NI | NI | | NI | | + | | NI | NI | NI | |
| 71G12 | | | | | | + | | | | | | | | | | | | | | | | | | | |
| D3S2405 | | NI | + | NI | − | − | | + | − | − | − | | + | NI | ++ | | NI | | | NI | | | | | |
| D3S1597 | − | NI | + | − | NI | − | − | + | | − | NI | − | NI | + | | | − | NI | + | + | NI | | | | |
| D3S2414 | + | NI | NI | − | − | − | NI | + | + | − | − | − | − | NI | NI | NI | | NI | − | + | + | − | | | |
| D3S1244 | NI | NI | NI | − | − | NI | NI | | NI | NI | − | NI | NI | | + | + | NI | − | NI | + | + | NI | NI | | |
| D3S3038 | NI | NI | + | − | + | − | NI | + | + | + | − | NI | NI | NI | | ++ | − | + | + | | + | | | + | NI |
| D3S1255 | | − | NI | − | NI | | − | | | NI | NI | NI | | | | | | + | − | | + | | | | |
| EABMD/H | + | − | NI | NI | NI | + | − | + | + | | − | NI | + | + | ++ | ++ | ++ | NI | NI | + | NI | | NI | − | NI |
| D3S2423 | NI | − | + | + | + | + | + | NI | + | NI | + | + | + | NI | + | − | | | | NI | | | NI | − | NI |
| D3S2396 | | − | | | | | + | | + | | | | | NI | + | − | | | | NI | | | NI | | |
| D3S1768 | + | + | NI | − | − | NI | + | NI | + | − | − | | − | NI | + | + | | + | NI | + | + | NI | + | NI | + |
| D3S1766 | | | | | | | | | + | | | | | | | | | | | | | | | | |
| 2C06 | | | | | | | | | NI | | | | | | | | | | | | | | | | |
| D3S2438 | | | | | | | | | | | | | | | | | | | | | | | | | |

− No Loss
+ LOH in Tumor Only
++ LOH in Tumor and Normal Adjacent TDLU
NI Not Informative
Data reported for "EABMD/H" represents the combined results for primers sets for EABMD and EABH (Table 2).

TABLE 2

Primers for LOH Analysis

LOCUS

FORWARD

| | | |
|---|---|---|
| D3S2397 | ATAGAGCCACACTTTGTCTCA | (SEQ ID NO:16) |
| 71G12 | CCTATCTCCATCTATTTATCTGTCT | (SEQ ID NO:18) |
| D3S2405 | TACCTTCCTTCCCCACTCTT | (SEQ ID NO:20) |
| D3S1597 | AGTACAAATACACACAAATGTCTC | (SEQ ID NO:22) |
| D3S2414 | CATTTTAGGTGGACGTCTGC | (SEQ ID NO:24) |
| D3S1244 | GTGCCCTTCCAGAGTT | (SEQ ID NO:26) |
| D3S3038 | CATCTTTCTTTTCCTGTTCCC | (SEQ ID NO:28) |
| D3S1255 | CTCACTCATGAACACAGATGC | (SEQ ID NO:30) |
| EABMD | AACGTTGGACCTCAAGCCCAT | (SEQ ID NO:32) |
| D3S2423 | TCTCTGGCTAAACATGATATATGG | (SEQ ID NO:34) |
| D3S2396 | ACCTCTTACTTGTGTTCTTGGG | (SEQ ID NO:36) |
| D3S1768 | GGTTGCTGCCAAAGATTAGA | (SEQ ID NO:38) |
| D3S1766 | ACCACATGAGCCAATTCTGT | (SEQ ID NO:40) |
| 2C06 | GTTGTACAGCCGACCAAGAT | (SEQ ID NO:42) |
| D3S2438 | GAAGAAACTTTCCCTCCTGC | (SEQ ID NO:44) |
| EABH | CATCTGAAATGCTGACCTGTT | (SEQ ID NO:46) |

REVERSE

| | | |
|---|---|---|
| D3S2397 | TCTTTGAGAACCACTGTCTCC | (SEQ ID NO:17) |
| 71G12 | AATCAGATCCCCTTGGAAAG | (SEQ ID NO:19) |
| D3S2405 | CAAACCAGAAGTGGGAGAGA | (SEQ ID NO:21) |
| D3S1597 | GCAAATCGTTCATTGCT | (SEQ ID NO:23) |
| D3S2414 | AACCACCATGTCACGTGTAT | (SEQ ID NO:25) |
| D3S1244 | AGTGAGGCATCCACTACC | (SEQ ID NO:27) |
| D3S3038 | GATACCATATTCAACATGAAGAGG | (SEQ ID NO:29) |
| D3S1255 | AACCCATCTTGTATTCTTGCAG | (SEQ ID NO:31) |
| EABMD | AGAATGCCAAGGAAGGGTGCA | (SEQ ID NO:33) |
| D3S2423 | TGGGATCCTGTCTCAAAAAA | (SEQ ID NO:35) |
| D3S2396 | TGACCAAGCCAGTATTGGAT | (SEQ ID NO:37) |
| D3S1768 | CACTGTGATTTGCTGTTGGA | (SEQ ID NO:39) |
| D3S1766 | ACCCAATTATGGTGTTGTTACC | (SEQ ID NO:41) |
| 2C06 | TACACATTCAGATTATGTGGGG | (SEQ ID NO:43) |
| D3S2438 | TCTCCTTGTCATCCTTCTGC | (SEQ ID NO:45) |
| EABH | AGCTGTCAGAACTAAGTGCTT | (SEQ ID NO:47) |

TABLE 3

Analysis of outcome in matched cases with and without 3pLOHn

| Case ID | Recur. type | mo. to recur/follow-up | 3pLOHn | age | Tumor Stage | Nodal Status |
|---|---|---|---|---|---|---|
| 4 | local | 42 | 1 | 54 | 2 | 1 |
| 20 | distant | 16 | 0 | 65 | 2 | 1 |
| 18 | distant | 77 | 0 | 60 | 2 | 1 |
| 25 | distant | 68 | 1 | 43 | 2 | 1 |
| 30 | none | 107 | 0 | 47 | 2 | 1 |
| 31 | none | 75 | 0 | 42 | 2 | 0 |
| 19 | local | 41 | 1 | 33 | 2 | 1 |
| 57 | none | 84 | 0 | 33 | 2 | 1 |
| 45 | none | 101 | 0 | 25 | 2 | 1 |
| 27 | none | 105 | 1 | 45 | 1 | 1 |
| 50 | none | 61 | 0 | 55 | 1 | 1 |
| 8 | local | 11 | 0 | 49 | 1 | 0 |
| 22 | distant | 19 | 1 | 44 | 1 | 1 |
| 38 | distant | 88 | 0 | 37 | 1 | 0 |
| 35 | none | 83 | 0 | 36 | 1 | 0 |
| 16 | local | 58 | 1 | 60 | 2 | 0 |
| 42 | none | 94 | 0 | 78 | 2 | 0 |
| 44 | none | 88 | 0 | 67 | 2 | 0 |
| 21 | distant | 14 | 1 | 54 | 2 | 0 |
| 33 | none | 69 | 0 | 46 | 2 | 0 |
| 34 | none | 74 | 0 | 45 | 2 | 0 |
| 12 | local | 108 | 1 | 63 | 1 | 0 |
| 5 | local | 33 | 0 | 68 | 1 | 0 |
| 28 | none | 95 | 0 | 64 | 1 | 0 |
| 10 | local | 57 | 1 | 58 | 1 | 0 |
| 32 | none | 78 | 0 | 53 | 1 | 0 |
| 43 | none | 72 | 0 | 46 | 1 | 0 |
| 15 | local | 67 | 1 | 53 | 1 | 0 |
| 40 | none | 81 | 0 | 47 | 1 | 0 |
| 41 | none | 78 | 0 | 46 | 1 | 0 |
| 53 | contralat | 48 | 1 | 39 | 1 | 0 |
| 13 | local | 36 | 0 | 45 | 1 | 0 |
| 39 | contralat | 91 | 0 | 39 | 1 | 0 |

TABLE 4

Analysis of 3pLOHn status in matched cases with and without recurrence in 5 yr. follow up

| Case ID | 5-yr recur | Recur. type | Mo to recur./FU | 3pLOHn | age | Tumor Stage | Nodal status |
|---|---|---|---|---|---|---|---|
| 20 | 1 | distant | 16 | 0 | 65 | 2 | 1 |
| 18 | 0 | distant | 77 | 0 | 60 | 2 | 1 |
| 33 | 0 | none | 69 | 0 | 46 | 2 | 1 |
| 4 | 1 | local | 42 | 1 | 54 | 2 | 1 |
| 30 | 0 | none | 107 | 0 | 47 | 2 | 1 |
| 25 | 0 | distant | 68 | 1 | 43 | 2 | 1 |
| 19 | 1 | local | 41 | 1 | 33 | 2 | 1 |
| 57 | 0 | none | 84 | 0 | 33 | 2 | 1 |
| 45 | 0 | none | 101 | 0 | 25 | 2 | 1 |
| 22 | 1 | distant | 19 | 1 | 44 | 1 | 1 |
| 50 | 0 | none | 61 | 0 | 55 | 1 | 1 |
| 27 | 0 | none | 105 | 1 | 45 | 1 | 1 |
| 16 | 1 | local | 58 | 1 | 60 | 2 | 0 |
| 42 | 0 | none | 94 | 0 | 78 | 2 | 0 |
| 44 | 0 | none | 88 | 0 | 67 | 2 | 0 |
| 21 | 1 | distant | 14 | 1 | 54 | 2 | 0 |
| 34 | 0 | none | 74 | 0 | 45 | 2 | 0 |
| 31 | 0 | none | 75 | 0 | 42 | 2 | 0 |
| 5 | 1 | local | 33 | 0 | 68 | 1 | 0 |
| 28 | 0 | none | 95 | 0 | 64 | 1 | 0 |
| 12 | 0 | local | 108 | 1 | 63 | 1 | 0 |
| 10 | 1 | local | 57 | 1 | 58 | 1 | 0 |
| 32 | 0 | none | 78 | 0 | 53 | 1 | 0 |
| 15 | 0 | local | 67 | 1 | 53 | 1 | 0 |
| 8 | 1 | local | 11 | 0 | 49 | 1 | 0 |
| 40 | 0 | none | 81 | 0 | 47 | 1 | 0 |
| 41 | 0 | none | 78 | 0 | 46 | 1 | 0 |
| 13 | 1 | local | 36 | 0 | 45 | 1 | 0 |
| 43 | 0 | none | 72 | 0 | 46 | 1 | 0 |
| 39 | 0 | contralat | 91 | 0 | 39 | 1 | 0 |
| 53 | 1 | contralat | 48 | 1 | 39 | 1 | 0 |
| 38 | 0 | distant | 88 | 0 | 37 | 1 | 0 |
| 35 | 0 | none | 83 | 0 | 36 | 1 | 0 |

TABLE 5

TRβ1 LOH, promoter methylation, and protein expression in primary breast tumors

| Case number | Patient age[2] | TRβ1 LOH in tumor | Promoter methylation[1] Tumor only | Promoter methylation[1] Tumor and peripheral | Pattern of nuclear TRβ1 in tumor cells (IHC)[3] |
|---|---|---|---|---|---|
| 385 | 44 | NI | Y | | + |
| 393* | 76 | Y | Y | | +/− |
| 396* | 49 | Y | Y | | − |
| 398* | 54 | NI | Y | | + |
| 1503 | 49 | Y | Y | | − |
| 1525 | 46 | Y | Y | | − |
| 368 | 90 | NI | | Y | − |
| 388 | 72 | Y | | Y | +/− |
| 394 | 43 | Y | | Y | − |
| 1500 | 72 | Y | | Y | +/− |
| 1522* | 78 | NI | | Y | + |

[1]Data represents combined results of COBRA and MSP analysis for all tumor samples.
*In these cases, tumor DNA displayed similar results by both methods of methylation analysis. Since non-overlapping CpG sites are amplified by the two methods, differences in methylation status were observed in the DNA from peripheral tissue (COBRA data shown here). This result suggests a greater increase in methylated sites within the tumor population as compared to the non-malignant tissue.
[2]Chi-square analysis of samples concordant by both methods show a significant association between patient age and TRβ1 methylation in peripheral tissue ($p \leq 0.05$).
[3]IHC, immunohistochemical detection of TRβ1 product in non-informative (NI) cases and those with LOH, gave a ($p \leq 0.025$).

TABLE 6

| Cell Culture | RT-PCR for TRβ1 | % Cells with TRβ1 < 3c | Methylated TRβ1 promoter MSP | Methylated TRβ1 promoter COBRA | RT-PCR for TRβ1 after 5-azaC |
|---|---|---|---|---|---|
| DU4475 | − | ND | | | |
| MDA435 | − | 43 | + | + | + |
| SKBR3 | − | 37 | + | + | + |
| MCF7 | + | 3 | − | − | +* |
| BT20 | + | 7 | | | |
| MDA157 | + | 11 | | | |
| MDA231 | + | 15 | | | |
| BT474 | + | 62 | − | − | |
| CAMA1 | + | 12 | − | − | |
| T47D | + | 6 | − | − | |
| Normal breast cell culture | + | 0 | | | |

*RT-PCR for MCF7 was the same before and after 5-aza C treatment

All publications and patent applications mentioned in this specification are herein incorporated by reference to the same extent as if each individual publication or patent application was specifically and individually indicated to be incorporated by reference.

What is claimed is:

1. A method for determining the likelihood of tumor reoccurrence in a patient previously diagnosed with a breast tumor, said method comprising:
   (1) providing a target cell sample from said patient, wherein said target cell sample comprises morphologically normal breast cells associated with the tumor, and wherein said target sample comprises a standardized volume to cell ratio, wherein the cells in said target sample are counted prior to microdissection and solubilization;
   (2) analyzing the target cell sample for loss of heterozygosity (LOH) at chromosomal locus 3p24.3;
   (3) classifying samples having LOH at chromosomal locus 3p24.3 as positive, wherein a positive sample indicates greater likelihood of tumor reoccurrence; and
   (4) identifying said positive sample to a clinician for prognosing and determining the course of treatment for said patient.

2. The method of claim 1, wherein the breast tumor cells have previously been determined to have LOH at 3p24.3.

3. The method of claim 1, wherein said patient has undergone a surgical procedure to treat said previously diagnosed breast tumor.

4. A method of determining post-surgical treatment for a breast cancer patient, said method comprising:
   (1) providing a target cell sample from said patient, wherein said target cell sample comprises morphologically normal breast cells associated with the breast cancer cells, and wherein said target sample comprises a standardized volume to cell ratio, wherein the cells in said target sample are counted prior to microdissection and solubilization;
   (2) analyzing the target cell sample for loss of heterozygosity (LOH) at chromosomal locus 3p24.3;
   (3) classifying samples having LOH at chromosomal locus 3p24.3 as positive, wherein a positive sample is an indicator that more aggressive post-surgical treatment is required; and
   (4) identifying said positive sample to a clinician for determining post-surgical treatment for said breast cancer patient.

5. The method of claim 4, wherein the breast tumor cells have previously been determined to have LOH at 3p24.3.

6. A method of identifying a patient as being at risk for breast cancer, said method comprising:
   (1) obtaining a breast tissue cell sample from said patient, wherein said breast tissue cell sample comprises a standardized volume to cell ratio, wherein the cells in said target sample are counted prior to microdissection and solubilization;
   (2) analyzing the breast tissue cell sample for loss of heterozygosity (LOH) at chromosomal locus 3p24.3;
   (3) classifying patients whose breast tissue cell sample exhibit LOH at chromosomal locus 3p24.3 as at risk of breast cancer; and
   (4) identifying said breast tissue cell sample exhibiting LOH to a clinician for prognosing and determining the course of treatment for said patient.

7. The method of claim 6, wherein said breast tissue cell sample is selected from the group consisting of nipple aspirate fluid, ductal lavage fluid, and breast tissue biopsy tissue.

8. A method for determining the likelihood of tumor re-occurrence in a patient previously diagnosed with a breast tumor, said method comprising:
   (1) providing a target cell sample from said patient, wherein said target cell sample comprises morphologically normal cells from tissue peripheral to the carcinoma cells;
   (2) analyzing the target cell sample for the level of expression of thyroid hormone receptor β1 compared to a control cell sample; and
   (3) classifying a target cell sample having a lower level of expression of thyroid hormone receptor β1 compared to the control cell sample as positive, wherein a positive sample indicates greater likelihood of tumor re-occurrence.

9. The method of claim 8, wherein the level of expression of thyroid hormone receptor β1 is determined by analyzing the amount of mRNA for thyroid hormone receptor β1.

10. The method of claim 8, wherein the level of expression of thyroid hormone receptor β1 is determined by analyzing the amount of thyroid hormone receptor β1 protein.

11. A method of determining post-surgical treatment for a breast cancer patient, said method comprising:
   (1) providing a target cell sample from said patient, wherein said target cell sample comprises morphologically normal cells from tissue peripheral to the carcinoma cells;
   (2) analyzing the target cell sample for the level of expression of thyroid hormone receptor β1 compared to a control cell sample; and
   (3) classifying a target cell sample having a lower level of expression of thyroid hormone receptor β1 compared to a control cell sample as positive, wherein a positive sample is an indicator that more aggressive post-surgical treatment is required.

12. The method of claim 11, wherein the level of expression of thyroid hormone receptor β1 is determined by analyzing the amount of mRNA for thyroid hormone receptor β1.

13. The method of claim 11, wherein the level of expression of thyroid hormone receptor β1 is determined by analyzing the amount of thyroid hormone receptor β1 protein.

14. A method of identifying a patient as at risk for breast cancer, said method comprising:
   (1) obtaining a breast tissue cell sample from said patient;
   (2) analyzing the breast tissue sample for the level of expression of thyroid hormone receptor β1 compared to a control cell sample; and
   (3) classifying a patient whose breast tissue cell samples have a lower level of expression of thyroid hormone receptor β1 compared to a control cell sample as at risk for breast cancer.

15. The method of claim 14, wherein said breast tissue cell sample is selected from the group consisting of nipple aspirate fluid, ductal lavage fluid, said breast tissue biopsy tissue.

16. The method of claim 14, wherein the level of expression of thyroid hormone receptor β1 is determined by analyzing the amount of thyroid hormone receptor β1 protein.

17. The method of claim 14, wherein the level of expression of thyroid hormone receptor β1 is determined by analyzing the amount of thyroid hormone receptor β1 protein.

* * * * *